United States Patent [19]

Knollmueller

[11] 4,048,084

[45] * Sept. 13, 1977

[54] FUNCTIONAL FLUID SYSTEMS CONTAINING ALKOXYSILANE CLUSTER COMPOUNDS

[75] Inventor: Karl O. Knollmueller, Hamden, Conn.

[73] Assignee: Olin Corporation, New Haven, Conn.

[*] Notice: The portion of the term of this patent subsequent to June 22, 1993, has been disclaimed.

[21] Appl. No.: 675,882

[22] Filed: Apr. 12, 1976

Related U.S. Application Data

[63] Continuation-in-part of Ser. No. 616,438, Sept. 24, 1975, Pat. No. 3,965,136.

[51] Int. Cl.$^2$ .............................................. C10M 3/46
[52] U.S. Cl. ................................................... 252/78.3
[58] Field of Search ................ 252/78.3; 260/448.8 A

[56] References Cited

U.S. PATENT DOCUMENTS

| | | | |
|---|---|---|---|
| 1,437,187 | 11/1922 | MacDonald | 252/73 |
| 1,952,105 | 3/1934 | Tseng | 252/73 |
| 3,965,136 | 6/1976 | Knollmueller | 252/78 X |

*Primary Examiner*—Harris A. Pitlick
*Attorney, Agent, or Firm*—F. A. Iskander; T. P. O'Day

[57] ABSTRACT

Functional fluid systems, i.e. hydraulic fluid and heat transfer fluid systems, containing alkoxysilane cluster compounds having the formula $RSi[OSi(OR')_3]_3$ wherein R is hydrogen, an alkyl, alkenyl, aryl or aralkyl group and each R' is independently selected from the same group as R with the proviso that at least a majority of R' radicals are sterically hindered alkyl groups having at least 3 carbon atoms, are described.

14 Claims, No Drawings

FUNCTIONAL FLUID SYSTEMS CONTAINING ALKOXYSILANE CLUSTER COMPOUNDS

This application is a continuation-in-part of co-pending U.S. application Ser. No. 616,438, filed Sept. 24, 1975 by the present inventor, now U.S. Pat. No. 3,965,136, entitled "Alkoxysilane Cluster Compounds and Their Preparation".

The present invention is directed to functional fluid systems containing specified fluids. More particularly, the present invention is directed to hydraulic and heat transfer fluid systems containing an effective amount of an alkoxysilane cluster compound, the compound being one having the general formula:

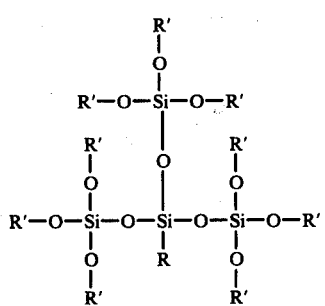

(I)

wherein R is hydrogen, an alkyl, aryl or aralkyl and each R' is independently selected from the same group as R with the proviso that at least a majority of R' radicals are sterically hindered alkyl groups having at least 3 carbon atoms. This general Formula (I) may also be written in an abbreviated form as $RSi[OSi(OR')_3]_3$ wherein R and R' are as defined.

Silicate esters, silanes and oxysilanes are well known for their utility as functional fluids and many of these compounds have been proposed for use as heat transfer fluids, hydraulic fluids, brake fluids, transmission fluids and the like. Novel alkoxysilane compounds with desirable functional fluid properties, which have heretofore not been described in the literature, are described in the above-identified parent application. The present invention is directed to the use of these compounds in functional fluid systems as more fully set forth below.

As mentioned, the compounds used in the functional fluid systems of the present invention are those represented by the Formula (I) above wherein R is hydrogen, an alkyl, alkenyl, aryl or aralkyl. Desirably, R is hydrogen, an alkyl or alkenyl having about 1 to about 18 carbon atoms or an aryl or aralkyl having about 6 to about 24 carbon atoms. Preferably, R is hydrogen, an alkyl having about 1 to about 8 carbon atoms or an aryl or aralkyl having about 6 to about 14 carbon atoms. In Formula (I), each R' is independently selected from the same group as R, with the proviso that at least a majority of the R' radicals are sterically hindered alkyl groups having at least 3 carbon atoms. The desired and preferred groups for R' are the same as for R subject to the preceeding proviso. Desirably, at least a majority of the R' radicals are sterically hindered alkyl groups having about 3 to about 24 carbon atoms and preferably are sterically hindered alkyl groups having about 4 to about 12 carbon atoms. By sterically hindered alkyl groups is meant alkyl radicals which contribute to the hydrolytic stability of the molecule, i.e. which inhibit the reaction of water with the silicon-oxygen or the carbon-oxygen bonds in the molecule. Exemplary of sterically hindered alkyl radicals are non-linear primary alkyl radicals having a beta position side chain of at least 2 carbon atoms, secondary alkyl radicals and tertiary alkyl radicals. Particularly useful sterically hindered alkyl groups include sec. butyl, isobutyl, 2-ethyl butyl, 2-ethyl pentyl, 3-ethyl pentyl, 2-ethyl hexyl, 3-ethyl hexyl, and 2,4-dimethyl-3-pentyl, etc.

The method of preparing the alkoxysilane cluster compounds used in the systems of the present invention is described in detail in parent application Ser. No. 616,438, filed Sept. 24, 1975 by the present inventor, and incorporated herein by reference.

The functional fluid systems to which the present invention is directed includes hydraulic type functional fluid systems and heat transfer type functional fluid systems.

The hydraulic type fluid systems include any system wherein a mechanical effort is converted to pressure at a first location, the pressure is transmitted from this first location to a second location via a hydraulic fluid, and the pressure is converted to a second mechanical effort at the second location. Thus, the hydraulic systems contemplated by the present invention include hydraulic brake systems, hydraulic steering mechanisms, hydraulic transmissions, hydraulic jacks and hydraulic lifts. Included among these are the hydraulic systems used in heavy equipment and transportation vehicles including highway and construction equipment, railways, planes and aquatic vehicles. Also included are special or custom fluid-requiring systems such as high pressure or temperature gradient systems including those employed in artic environments as well as those found in aerospace and lunar vehicles and the like.

The heat transfer type fluid systems include the hydraulic systems described above wherein heat is dissipated by the hydraulic fluid and include many other systems as well. In general, the present invention contemplates heat transfer systems wherein heat is passed from a first heat conductor at a first location to a heat transfer fluid, the heat is transmitted from the first location to a second location via the heat transfer fluid, and the heat is passed from the heat transfer fluid to a second conductor at the second location. Thus, the heat transfer systems of the present invention include heat dissipation systems, fluidic heating systems, e.g. radiator type circulating fluid heating systems, heat exchange systems such as gas-liquid and liquid-liquid concurrent and countercurrent tubular heat exchangers as are used, for example, in the chemical process industries, cooling systems for nuclear reactors, radiator type cooling systems, and any other temperature gradient systems in which a closed or sealed fluid heat transfer medium is used.

In the functional fluid systems of the present invention, the compounds of Formula (I) above are used in an effective amount. Due to the particularly advantageous hydrolytic stability of these compounds, as well as their high lubricity and low viscosity indices, the compounds may be used without any additives or diluents. Thus, by an effective amount of these compounds is meant the compound product without additional components as well as fluids containing additional fluid components. In one embodiment, the compounds of Formula (I) may be employed without additives or diluents. Alternatively, these compounds may comprise the base component of a functional fluid or may constitute a minor component, e.g. an additive, in a functional fluid containing a different base component. In general, an effective amount may be any amount which will produce the desired fluid characteristics for a given system. Therefore, as little as 5% or less of one or more of the compounds of Formula (I) may be used or as much as about 100% of the compounds may be used, percentages by weight. For example, 20% to about 95% or about 100% of the functional fluid may be one or more of the compounds of Formula (I), e.g. 45% to 90% of the fluid may comprise one or more compounds of Formula (I).

Various diluents, inhibitors and other additives are well known in the functional fluid art and these may optionally be added to the functional fluids used in the systems of the present invention, if desired. For example, a diluent component may be one or more glycol monoethers or diethers of the formula:

wherein $R_1$ is an alkyl of 1 to 4 carbon atoms, $R_2$ is alkylene of 2 to 4 carbon atoms, $R_3$ is hydrogen or an alkyl of 1 to 4 carbon atoms and $x$ is an integer from 2 to 4. The $R_1$, $R_2$ and $R_3$ groups may be straight chained or branched and the alkylene oxide group $OR_3$ in the above formula may comprise mixtures of alkylene oxides. Also included among the possible diluents are one or more glycols, such as the alkylene glycols, having the formula:

wherein $R_4$ is an alkylene of 2 to 3 carbon atoms and $y$ is an integer from 1 to 5.

Illustrative of the above-described diluents are the following: diethylene glycol monoethyl ether, diethylene glycol monobutyl ether, triethylene glycol monomethyl ether, triethylene glycol monoethyl ether, tetraethylene glycol monomethyl ether, ethylene glycol, propylene glycol, diethylene glycol and tetraethylene glycol. Various other diluents and mixtures thereof, which are well known in the art may also be used with the organosilane containing base component of this invention. U.S. Pat. No. 3,377,288 discloses various diluents which may be utilized.

Generally, the particular amount of diluents which is used is not critical and widely varying amounts may be used. More particularly, the diluent components may constitute from 0 up to about 80 percent by weight of the fluid and preferably from about 20 to about 60 percent.

Various additives may be added to the fluids used in the systems of this invention to control or modify various chemical and physical properties. Among the various types of additives which can be added to the fluids are included inhibitors for pH and corrosion control, antioxidants, rust inhibitors, viscosity index improvers, pour point depressants, lubricating additives, antifoamants, stabilizers, vapor phase corrosion inhibitors, rubber swelling adjusters, demulsifiers, dyes and odor suppressants. Generally, the total amount of additives which may be incorporated into the fluid composition will vary between about 0 to about 20 percent, e.g. from about 0.1 to 8 percent and more specifically from about 0.2 to about 5 percent by weight, based on the total weight of the fluid composition.

For example, alkaline inhibitors for pH and corrosion control may optionally be employed in an amount sufficient to maintain alkaline conditions in the fluid compositions, e.g. at an apparent pH value of from about 7.0 to about 11.5, if desired. These inhibitors may generally be added in an amount of from about 0 to about 8 percent by weight based on the total weight of fluid compositions, e.g. from about 0.5 to about 6 percent. Useful alkaline inhibitors include, for example, alkali metal salts of higher fatty acids such as potassium oleate, the potassium soap of rosin or tall oil fatty acids, amines such as morpholine and ethanolamine and amine salts such as mono- or dibutyl ammonium borates.

An antioxidant may optionally be used, if desired. Typical antioxidants include, 2,2,-di-(4-hydroxyphenyl)propane, phenothiazine, amines such as phenyl-alpha-napthylamine and hindered phenols such as dibutyl cresol. Generally, the amount of antioxidant used will vary from 0 to about 3 percent by weight, e.g. from about 0.001 to about 2 percent by weight based on the total weight of the fluid composition.

Additionally, other additives, if desired, may be incorporated into the fluid composition. For example, corrosion inhibitors such as butynediol and rubber swelling adjusters such as dodecyl benzene may be used.

The above-noted inhibitors and additives are merely exemplary and are not intended as an exclusive listing of the many well-known materials which can be added to fluid compositions to obtain various desired properties. Other illustrations of additives and diluents which may be used can be found in U.S. Pat. No. 3,377,288 and in "Introduction to Hydraulic Fluids" by Roger E. Hatton, Reinhold Publishing Corp. (1962).

The following examples illustrate various embodiments of the present invention, but the present invention should not be construed to be limited thereto. The compounds described in the following examples are prepared as described in the examples of parent application Ser. No. 616,438, filed Sept. 24, 1975 by the present inventor, and incorporated herein by reference.

EXAMPLE 1

A functional fluid was prepared comprising a compound having the formula:

The compound fluid was tested for various functional fluid properties. To examine an important aspect of its heat transfer properties, the fluid was tested to determine its ASTM slope (ASTM test no. D 341—43). The ASTM slope is based on viscosity measurements at 100° F. and 210° F. and is used as an indication of change in viscosity in response to temperature changes. This fluid exhibited an ASTM slope of 0.45, one which is very good for functional fluids and particularly for one containing no viscosity controlling additives. Also, the lubricity properties of the fluid were tested by subjecting the fluid to a wear scar test in which a four ball 40 kg load apparatus is used at 1800 rpm and 168° F. for 1 hour. This fluid yielded a wear scar test result of 0.73 mm total scar, illustrating very good lubricity for a fluid containing no lubricity improver. One significant test for a hydraulic fluid is its stability in the presence of water. This fluid was subjected to a hydrolysis solids test which was carried out at 210° F. in the presence of 33% by weight water and copper metal catalyst for 100 hours. Only 0.002% solids was found to be present at the end of the test. In addition to the above desirable characteristics, this fluid exhibited a flash point of 390°

F. suggesting its use as a hydraulic fluid under severe high thermal conditions. Low temperature functional fluid utility was also suggested by the fact that the fluid was still liquid at temperatures lower than −40° F. (Viscosity measurements: 10 centistokes at 210° F.; 37.2 cs at 100° F.; 1050 cs at −40° F.) The ASTM extended viscosity index (ASTM test no. D 22 70) was found to be 310. Weight loss in air was found to be only 13.96% at 1 atmosphere, 400° F. for 1 hour.

The above tests were repeated for the fluids of Examples 2 through 4, as follows:

Example 2

| Fluid | HSi[OSi(sec. $C_4H_9O)_3]_3$ |
|---|---|
| Viscosity: | |
| at 210° F. | 8.02 cs |
| at 100° F. | 26.1 cs |
| at −40° F. | 544.8 cs |
| ASTM Slope | 0.46 |
| Extended Viscosity Index | 322 |
| Wear Scar | 0.98 mm |
| % Solids After Hydrolysis | <0.005 |
| Weight Loss in Air Test | 19.16 |
| Flash Point | 380° F. |

Example 3

| Fluid | $C_2H_5Si[OSi(sec. C_4H_9O)_3]_3$ |
|---|---|
| Viscosity: | |
| at 210° F. | 12.33 cs |
| at 100° F. | 45.21 cs |
| at −40° F. | 1505 cs |
| ASTM Slope | 0.44 |
| Extended Viscosity Index | 300 |
| Wear Scar | 0.57 mm |
| % Solids After Hydrolysis | 0.01 |

Example 4

| Fluid | $CH_2CHSi[OSi(sec. C_4H_9O)_3]_3$ |
|---|---|
| Viscosity: | |
| at 212° F. | 11.04 cs |
| at 100° F. | 42.7 cs |
| at −40° F. | Frozen |
| ASTM Slope | 0.47 |
| Extended Viscosity Index | 270 |
| Wear Scar | 0.70 mm |
| % Solids After Hydrolysis | 0.03 |

What is claimed is:

1. In a method wherein a first mechanical effort is converted to pressure at a first location, the pressure is transmitted from said first location to a second location via a hydraulic fluid, and said pressure is converted to a second mechanical effort at said second location, the improvement which comprises using as said hydraulic fluid one which comprises an effective amount of a compound having the formula:

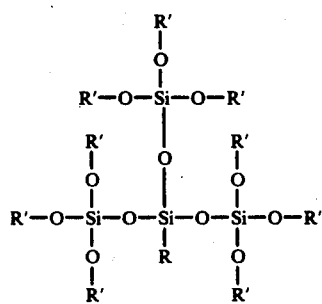

(I)

wherein R is hydrogen, an alkyl, alkenyl, aryl or aralkyl, and each R' is independently selected from the same group as R with the proviso that at least a majority of R' radicals are sterically hindered alkyl groups having at least 3 carbon atoms.

2. The method of claim 1 wherein R is hydrogen, an alkyl or alkenyl having about 1 to about 18 carbon atoms or an aryl or aralkyl having about 6 to about 24 carbon atoms and wherein each R' is independently selected from the same group as R, subject to the above proviso.

3. The method of claim 2 wherein a majority of the R' radicals are sterically hindered alkyl groups having about 3 to about 24 carbon atoms.

4. The method of claim 1 wherein R is hydrogen, an alkyl having about 1 to about 8 carbon atoms or an aryl or aralkyl having about 6 to about 14 carbon atoms and wherein each R' is independently selected from the same group as R, subject to the above proviso.

5. The method of claim 4 wherein a majority of the R' radicals are sterically hindered alkyl groups having about 4 to about 12 carbon atoms.

6. The method of claim 1 wherein a majority of the R' radicals are sterically hindered alkyl groups having about 3 to about 24 carbon atoms.

7. The method of claim 6 wherein a majority of the R' radicals are sterically hindered alkyl groups having about 4 to about 12 carbon atoms.

8. In a method wherein heat is passed from a first heat conductor to a heat transfer fluid at a first location, the heat is transmitted from said first location to a second location via said heat transfer fluid, and said heat is passed from said heat transfer fluid to a second heat conductor at said second location, the improvement which comprises using as said heat transfer fluid one which comprises an effective amount of a compound having the formula:

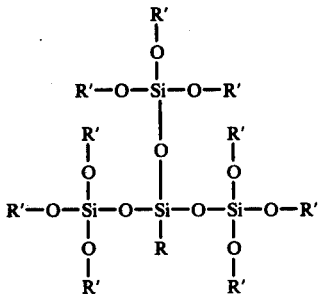

(I)

wherein R is hydrogen, an alkyl, alkenyl, aryl or aralkyl, and each R' is independently selected from the same group as R with the proviso that at least a majority of R' radicals are sterically hindered alkyl groups having at least 3 carbon atoms.

9. The method of claim 8 wherein R is hydrogen, an alkyl or alkenyl having about 1 to about 18 carbon atoms or an aryl or aralkyl having about 6 to about 24 carbon atoms and wherein each R' is independently selected from the same group as R, subject to the above proviso.

10. The method of claim 9 wherein a majority of the R' radicals are sterically hindered alkyl groups having about 3 to about 24 carbon atoms.

11. The method of claim 8 wherein R is hydrogen, an alkyl having about 1 to about 8 carbon atoms or an aryl or aralkyl having about 6 to about 14 carbon atoms and wherein each R' is independently selected from the same group as R, subject to the above proviso.

12. The method of claim 11 wherein a majority of the R' radicals are sterically hindered alkyl groups having about 4 to about 12 carbon atoms.

13. The method of claim 8 wherein a majority of the R' radicals are sterically hindered alkyl groups having about 3 to about 24 carbon atoms.

14. The method of claim 13 wherein a majority of the R' radicals are sterically hindered alkyl groups having about 4 to about 12 carbon atoms.

* * * * *